United States Patent [19]

Hall et al.

[11] 3,947,468

[45] Mar. 30, 1976

[54] PRODUCTION OF DIBENZOPYRANS, THEIR ISOMERIC FLUORENOLS AND DIBENZOTHIOPYRANS

[75] Inventors: Walter L. Hall, Mount Vernon, Ind.; Jimmy L. Webb, Jonesville, N.Y.

[73] Assignee: General Electric Company, Schenectady, N.Y.

[22] Filed: June 29, 1973

[21] Appl. No.: 374,906

Related U.S. Application Data

[63] Continuation-in-part of Ser. No. 147,163, May 26, 1971, abandoned.

[52] U.S. Cl. ....... 260/327 TH; 260/345.3; 260/516; 260/520 D; 260/609 D; 260/619 F; 252/404
[51] Int. Cl.$^2$ ...................................... C07D 311/82
[58] Field of Search .......... 260/328, 327 TH, 345.3, 260/514, 619 F, 609 D, 516, 520

[56] References Cited
OTHER PUBLICATIONS
Rigby, C. A., Vol. 74: 125035z, 1971.

Primary Examiner—Henry R. Jiles
Assistant Examiner—C. M. S. Jaisle
Attorney, Agent, or Firm—F. Wesley Turner; Joseph T. Cohen; Jerome C. Squillaro

[57] ABSTRACT

Phenols and thiophenols having an ortho-phenyl substituent react with most aldehydes and ketones in very strongly acidic liquid media to form a dibenzopyran or dibenzothiopyran. The dibenzopyrans, but not the dibenzothiopyrans, can be isomerized to their corresponding fluorenols. The pyran or thiopyran ring can be cleaved chemically or electrochemically to produce phenols and thiophenols which have an ortho substituent in the ortho position of the phenyl substituent of the starting phenol or thiophenol which is characteristic of the aldehyde or ketone reactant. These products as well as the fluorenols, being phenolic bodies, are useful as stabilizers and antioxidants.

18 Claims, No Drawings

PRODUCTION OF DIBENZOPYRANS, THEIR ISOMERIC FLUORENOLS AND DIBENZOTHIOPYRANS

This application is a continuation-in-part of our formerly copending application, Ser. No. 147,163, filed May 26, 1971, now abandoned, and assigned to the same assignee as the present invention.

This invention relates to a process for making dibenzopyrans, their isomeric fluorenols, mixtures of said dibenzopyrans and fluorenols or dibenzothiopyrans by reaction of either a ketone or aldehyde with a benzenoid compound having at least one phenolic hydroxyl or mercaptan substituent and at least one

substituent ortho to the phenolic hydroxyl or mercaptan group. In this reaction, the pyran or thiopyran ring is formed by bridging the oxygen of the phenolic hydroxyl group or the sulfur of the mercaptan group to the ortho position of the o-phenyl substituent by means of the carbon atom of the carbonyl group of the aldehyde or ketone. This ring closing reaction is effected in a very strongly acidic liquid phase. Under the reaction conditions, the dibenzopyrans, but not the dibenzothiopyrans, can be isomerized, if desired, to their corresponding fluorenols, if the meta position involved in the isomerization, has a displaceable substituent, generally hydrogen.

In our studies of the chemistry of 2,6-diphenylphenol, we found that this phenol, unlike almost all other phenol, did not react with aldehydes or ketones in the presence of the usual mineral acid catalysts to form bisphenols. This confirms the finding of J. Kahovec and J. Popisil, "Coll. Czechoslov. Chem. Comm." 34, 2483 (1969) that this phenol does not react with acetone in the presence of the usual acid catalysts. Generally, no useful reaction occurs unless an inert medium is used whose acid strength, as measured on the Hammett $H_o$ scale, is at least as strong as undiluted or neat trifluoroacetic acid. Under these very strong conditions, the particular product is dependent on the acid strength, the duration of the reaction, the temperature, the solubility of the product, the aldehyde or ketone and whether the phenol is 2,6-diphenylphenol or its isologue 2,6-diphenylthiophenol. Although 2-phenylphenol will react with aldehydes and ketones in the presence of the usual mineral acid catalysts to form bisphenols, the yield is generally quite low. When we studied this phenol under our very strong acid conditions, we found that it usually gave dibenzopyrans. We further found that this was true of any phenol including thiophenols having a phenyl substituent in at least one of the two positions ortho to the phenolic hydroxyl or mercapto group. A few aldehydes and ketones did produce bisphenols with 2,6-diphenylphenol. Under the very strongly acid conditions, alkyl groups having a tertiary α-carbon atom, i.e., there is no hydrogen on the carbon atom adjacent to the phenyl nucleus, tend to either migrate to the para or 4-position or dealkylate, but this does not interfere with the main reaction leading to the formation of the pyran or thiopyran ring. The various products obtained and the conditions to obtain them are more fully discussed in the following applications filed together with the parent application and assigned to the same assignee as the present invention and which are hereby incorporated by reference.

Unlike other aldehydes and ketones, formaldehyde and acetaldehyde, preferably as their polymeric modifications, react in the presence of formic acid and trifluoroacetaldehyde, preferably as its hydrate, 1,1,1-trifluoroacetone, hexafluoroacetone and glyoxylic acid react under the above stronger acidic conditions with 2,6-diphenylphenol to form very good yields of the corresponding bisphenols. These bisphenols are disclosed and claimed in our formerly copending application, Ser. No. 147,165, filed May 26, 1971 now U.S. Pat. No. 3,739,035.

These same aldehydes and ketones did not give bisphenols with 2,6-diphenylthiophenols. Instead, the products were bisthioethers (thioacetals) except in the case of glyoxylic acid where the product was a dibenzothiopyran. Both 2,6-diphenylphenol and its thio isologue yield dibenzopyrans or dibenzothiopyrans with other aldehydes and ketones except for completely aromatic ketones which do not react at all. These dibenzopyrans, dibenzothiopyrans and the isomeric fluorenols of the dibenzopyrans are new chemical compounds and are disclosed and claimed in our formerly copending application, Ser. No. 147,164, filed May 26, 1971, now U.S. Pat. No. 3,728,465.

Diketones in which there is at least one alkyl group attached to each ketonic carbonyl group, will react under these same conditions to form bis(dibenzopyrans) which can be isomerized to their corresponding bisfluorenols. These are new chemical compounds and are disclosed and claimed in our formerly copending application, Ser. No. 147,162, filed May 26, 1971, now U.S. Pat. No. 3,821,317.

In addition to producing the above-described new compounds, our reaction, which is the subject of the present invention, can be used to prepare a much wider range of dibenzopyrans, dibenzothiopyrans and fluorenols, many of which are known in the art, but are very difficult to prepare or require exotic starting materials which are difficult to obtain. For example, R. S. Cahn in a study on the structure of cannabinol, desired to make what he called 2:2-dimethyldibenzopyran, but which, by present nomenclature is called 6,6-dimethyl-6H-dibenzo[b,d]pyran having the formula:

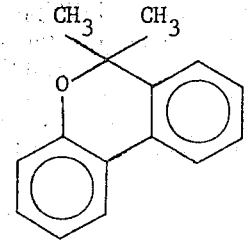

He reports in J. Chem. Soc., 1933, 1400, that to synthesize this compound, he first had to prepare the δ-lactone of 2'-hydroxy-2-biphenylenecarboxylic acid. His initial attempts to prepare this lactone by reaction of magnesium with o-bromophenyl-o-bromobenzoate or by diazotization of phenyl anthranilate failed. He was able to make it in 22 percent yield by reaction of phenol with anthranilic acid diazonium sulfate. The lactone was reacted with an excess of methyl magnesium iodide to give an almost quantitative yield of 2'-hydroxy-2-biphenylisopropanol, also known as o-(o-hydroxyphenyl)-α,α-dimethylbenzyl alcohol. This latter compound was dehydrated in about 90 percent yield to the desired pyran. He also made the 2-methyl homologue of the pyran by using p-cresol in place of phenol. M. Anchel and A. H. Blatt reported in J. Am. Chem. Soc., 63, 1948 (1941), that Cahn was mistaken when he reported that the 2,6,6-trimethyl-6H-dibenzo[b,d]-pyran, when heated with a mixture of hydrochloric and acetic acids, underwent opening of the pyran ring and loss of acetone to form 2-hydroxy-5-methylbiphenyl. The showed that instead the product was 1,9,9-trimethyl-4-fluorenol, the fluorenol isomer of the above trimethyldibenzopyran. They also showed that the fluorenol could be obtained directly from the 2'-hydroxy-5'-methyl-2-biphenylisopropanol by heating it with the mixture of hydrochloric and acetic acids in a sealed tube at 200°. The yield increased and then decreased with time being 35, 71, 68 and 51 percent after 8, 24, 31 and 48 hours, respectively. If the heating was stopped at the end of 30 minutes, an 80 percent yield of the pyran was obtained.

In marked contrast to the above involved procedures, our process can make the same pyrans or fluorenols from acetone and o-phenylphenol or 4-methyl-2-phenylphenol. The pyrans are obtained in greater than 90 percent yield by a single step reaction at reflux temperature for 48 hours using trifluoroacetic acid as the liquid reaction medium. The fluorenols are obtained in greater than 90 percent yield by a single step reaction (no isolation of pyran intermediate) at room temperature for 1.5 hours using liquid hydrogen fluoride as the reaction medium. They can also be obtained from the isolated pyran by heating in the strongly acidic medium or by using a Lewis acid, for example, AlCl$_3$, BF$_3$ in trifluoroacetic acid, etc.

Using the above reaction of o-phenylphenol and acetone as illustrative of our reaction in its simplest aspects, it can be illustrated by the general equation:

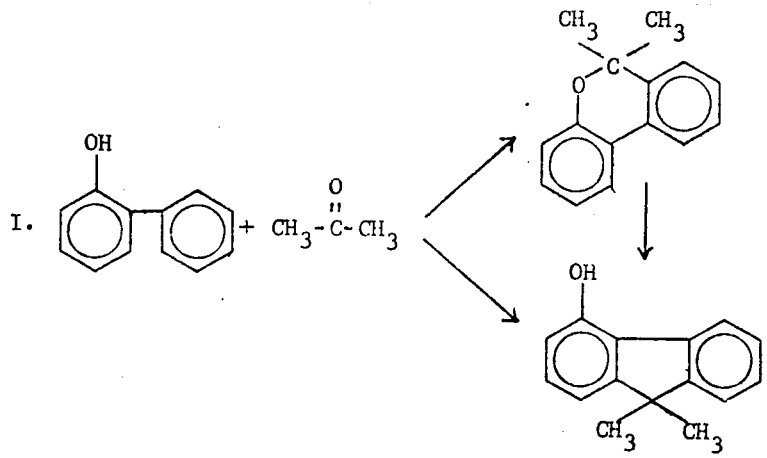

When the initial benzenoid compound has a phenyl substituent having an unsubstituted ortho position in each of the two positions ortho to the phenolic hydroxyl group, either phenyl substituent can be involved in the initial reaction to form the benzopyran ring. After isomerization of the dibenzopyran to the corresponding fluorenol, the second phenyl substituent is again ortho to the hydroxyl group and can now be further reacted with an aldehyde or ketone to produce another pyran ring forming an indenodibenzopyran (alternatively known as a benzopyranofluorene and as a benzofluorenopyran) which, in turn, can be isomerized to the corresponding indenofluorenol, which itself can be formed directly without isolation of the pyran, as described above.

This further reaction is illustrated by the following equation, using 2,6-diphenylphenol and acetone as illustrative examples, and assuming that the above-illustrated reaction of acetone with 2,6-diphenylphenol to first form 9,9-dimethyl-3-phenyl-4-fluorenol has been effected:

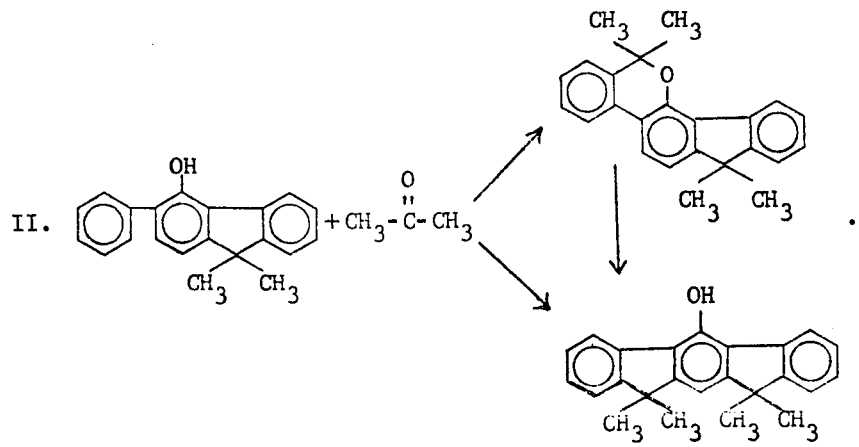

If an excess of acetone is used with 2,6-diphenylphenol, all four possible products can be found in the reaction mixture with the amount of each being dependent on the acidity of the reaction medium, time of reaction and temperature of reaction.

It is also possible to have a benzenoid compound having up to four hydroxyl or mercaptan groups each having at least one phenyl substituent ortho to it, i.e., on the ring carbon atom adjacent to the carbon atom bearing the phenolic hydroxyl or mercapto group. It is also possible to have a hydroxyl substituent on the phenyl substituent of the phenol so that each phenyl ring is ortho to a phenolic hydroxyl group, e.g., o,o'-biphenol, etc. Likewise, it is possible to have an aldehyde with more than one formyl group, a ketone with more than one ketonic carbonyl group or a mixed aldehyde-ketone having at least one formyl group and at least one ketonic carbonyl group. When such reactants are used in our reaction, all of the possible products, for example, bis(dibenzopyrans), bis(dibenzothiopyrans), bis(fluorenols), bis(indenodibenzopyrans), bis(indenofluorenols), tris(dibenzopyrans), tetrakis(dibenzopyrans), benzopyranobenzopyrans, quaterpyrano-p-terphenyl, etc., including polymers, can be made. As will be readily appreciated, as the number of phenyl substituents ortho to one or more phenolic hydroxyl or mercaptan groups increases or as the number of phenolic hydroxyl or mercaptan groups ortho to one or more phenyl substituents increases, the number of reactive sites (i.e., sites involved in a ring formation producing either a benzopyrano or indeno derivative of the benzenoid compound) increases and consequently the number of products increases, some being isomers. This greatly increases the separation problem unless the desired product is that obtained by reaction of all of the active sites and by driving the reaction to completion. Even this becomes more difficult as the number of reactive sites increases and, in some cases a single product is not possible. No steric hinderance has been found. The most sterically hindered phenolic hydroxyl group would be that found in 2,6-diphenylphenol, yet as Example 1 illustrates the four possible products are present and can be separated and isolated as individual products. Where these further reactions are not desired, they can be suppressed by techniques well-known in the art, for example, by using an excess of the carbonyl compound, less acidic reaction conditions, lower temperature, shorter reaction time, etc. See also, Examples 18, et seq.

When it is desired to prepare the higher condensation products, for example the fluorenols (except for those that will not condense further), indenodibenzopyrans, indenofluorenols, etc., in highest yields and purity, we prefer to first form a dibenzopyran precursor and isolate it from the reaction mixture and then isomerize it to the fluorenol in the absence of the aldehyde or ketone reactant. The isolated fluorenol, if it has a phenyl substituent ortho to the hydroxyl group, can then be reacted to the higher condensed products if desired. It is obvious that no isomerization of the dibenzopyran to the fluorenol can occur when the initial phenol has a nondisplaceable substituent in the meta position involved in the isomerization. For example, 2,3-diphenylphenol and 2,3-diphenylhydroquinone will only yield the dibenzopyran products, but the other diphenylphenols or diphenylhydroquinones yield both dibenzopyran and fluorenol products.

The benzenoid compounds which we prefer to use for our reaction are those benzenoid compounds having at least one -XH substituent on the benzene ring which is ortho to at least one

substituent, any other substituents for the hydrogen on the ring carbons of the benzenoid compound being lower alkyl, $C_{4-8}$-cycloalkyl, phenyl, lower alkyl substituted phenyl, $C_{4-8}$-cycloalkyl substituted phenyl, halogen, -XR,

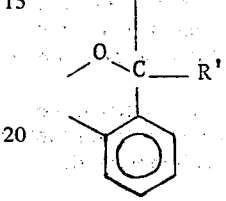 .or 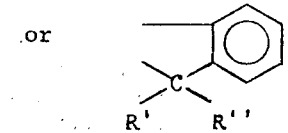 , the two free valences of the last two substituents being connected to adjacent ring carbon atoms of said benzenoid compound with the proviso that the free valence attached to the ring carbon atom of the last substituent be connected to a ring carbon atom ortho to an -OH substituent on the ring of said benzenoid compound, where X is oxygen or sulfur, R is hydrogen, lower alkyl, $C_{4-8}$-cycloalkyl or phenyl, R' and R'', taken together with the carbon atom to which both are attached, is cyclohexyl or lower alkyl substituted cyclohexyl, and, individually, R' is hydrogen, lower alkyl or $C_{4-8}$-cycloalkyl, lower haloalkyl or $C_{4-8}$-halocycloalkyl, wherein the α-carbon atom of said substituents, other than the hydrogen, has at least one hydrogen and no more than one halogen and R'' is alkyl, cycloalkyl, haloalkyl or halocycloalkyl, as defined for R' and, in addition, phenyl or substituted phenyl wherein the substituents are lower alkyl, $C_{4-8}$-cycloalkyl, halo or nitro, there being no more than one nitro group on any one phenyl ring. The maximum number of -XH substituents is five which means that there would be only one

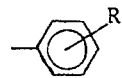

(R-phenyl) substituent, but if both of its ortho positions were unsubstituted they could both be involved in the pyran ring forming reaction with the two -XH substituents ortho to the R-phenyl substituent. The maximum number of -XH substituents that can be ortho to an R-phenyl substituent is four and requires two R-phenyl substituents which would be in the para position with respect to each other. For a fluorenol to be formed, the maximum number of -OH or R-phenyl substituents is four of either and their total can not be greater than 5. In view of the complexity of the reaction and the mixture of products obtained as the number of reactive sites increases, we prefer those benzenoid compounds having one or two -XH substituents and one or two R-phenyl substituents ortho to at least one of the -XH substituents, preferably one or two R-phenyl substituents ortho to each said -XH substituent, i.e., there can be one to two -XH substituents and one to four R-phenyl substituents where X and R are as defined previously.

For the benzenoid compound to form a dibenzopyran which can isomerize to a fluorenol, it must have at least one R-phenyl substituent with an -OH substituent ortho to it and the other position, which is ortho to it and meta to the -OH, must have a substituent which is replaceable under the strongly acidic reaction conditions, for example, a tertiary alkyl group which migrates or dealkylates. Preferably the replaceable substituent is hydrogen, i.e., the position is unsubstituted. It will be apparent from the structures involved that two is the maximum number of benzopyrano substituents on the benzenoid compound that can isomerize, e.g., the starting material for our reaction could be 2,6-diphenylphenol, which could have any of the various other substituents in the 4 position, 3,6-diphenylcatechol, 2,4-diphenylresorcinol, 2,5-diphenylhydroquinone, etc. In this regard, see equation II and Examples 1, 4-6 and 30.

Of the above preferred benzenoid compounds, we prefer to use as starting materials for our reaction the simple phenols, either the monohydric phenols or thiophenols having the formula,

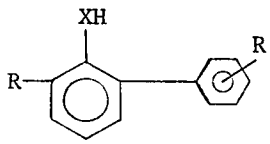

or the dihydric phenols, thiophenols or mixed phenol-thiophenols having the formula,

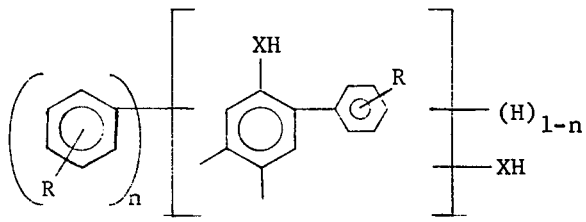

where R and X are as previously defined and n is 0 or 1.

These can be described as benzenoid compounds having one or two -XH substituents and one or two

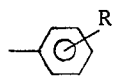

substituents ortho to at least one of said -XH substituents where R and X are as previously defined.

The aldehydes and ketones or mixed aldehyde-ketones which we prefer to use are those mono- or dicarbonyl compounds having no more than 20 carbon atoms, each carbonyl moiety being either ketonic directly attached to no more than one aromatic carbon atom (i.e., is not a completely aromatic ketone), or aldehydic, there being at least two carbon atoms between each carbonyl moiety of said dicarbonyl compound, each remaining moiety, which is attached directly to the carbon atom of said carbonyl moiety, being (a) saturated, monovalent or divalent, aliphatic hydrocarbon (i.e., alkyl, cycloalkyl, alkylene or cycloalkylene) or halohydrocarbon (i.e., haloalkyl, halocycloalkyl, haloalkylene, or halocycloalkylene) in which each carbon atom that is attached to the carbon atom of said carbonyl moiety has at least one hydrogen and no more than one halogen attached thereto, (b) phenyl, phenylene, substituted phenyl or substituted phenylene wherein the phenyl and phenylene substituents are lower alkyl, $C_{4-8}$ cycloalkyl, halogen or nitro, there being no more than one nitro group on any one phenyl ring or (c) combinations of (a) and (b). In addition, glyoxylic acid can be the carbonyl compound when X of the benzenoid compound is sulfur.

The alkylene and haloalkylene moieties can join two carbonyl groups to form acyclic aldehydes, acyclic ketones or cyclic ketones, i.e., have one of the formula

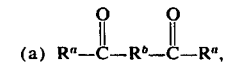 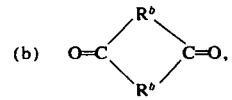

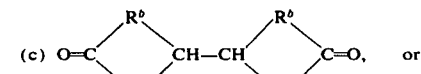

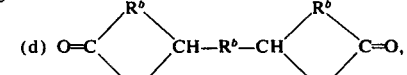

where $R^a$ is the same as previously defined for $R''$ and, in addition hydrogren, $R^b$ is lower alkylene or lower haloalkylene and each has at least two carbon atoms between the two carbonyl groups.

From the above discussion, it is thus seen that the mono- and dicarbonyl compounds can also be described as a mono- or dicarbonyl compound having no more than 20 carbon atoms, each carbonyl group being ketonic or formyl, there being at least two carbon atoms between each carbonyl moiety of said dicarbonyl compound, said mono- or dicarbonyl compound: (a) being glyoxylic acid, but only when the -XH group of the compound of A is -SH, or (b) having one of the formulae:

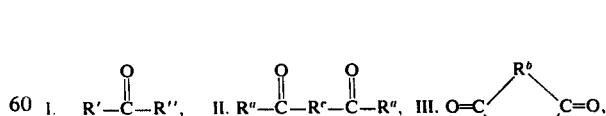

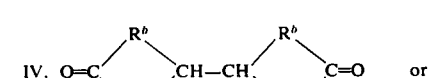

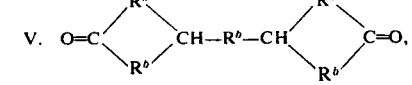

where R' and R'' are as defined above, $R^a$ is the same as R'' and, in addition, hydrogen, $R^b$ is (1) lower alkylene, (2) lower haloalkylene, both (1) and (2) having at least one hydrogen and no more than one halogen on the carbon atom alpha to the carbonyl groups, and $R^c$ is the same as $R^b$ and, in addition, when $R^a$ is other than phenyl or substituted phenyl, phenylene or substituted phenylene wherein the substituents are lower alkyl, $C_{4-8}$-cycloalkyl, halogen or nitro, there being no more than one nitro group on any one phenyl ring.

From what has been said above and the above definitions off R' and R'', it is obvious that the above benzenoid compounds having R' and R'' in their formulae, are actually initial dibenzopyran or fluorenol products of our reaction which are being further condensed to the higher condensed products described above.

Typical examples of lower alkyl and $C_{4-8}$-cycloalkyl substituents which can be present on the benzenoid compound or as the -R group on the phenyl and -X- substituents of the benzenoid compound are: methyl, ethyl, propyl, isopropyl, the various acyclic and cyclic butyl groups, i.e., n-butyl, sec-butyl, 2-methylpropyl, tert-butyl, cyclobutyl, etc., the various acyclic and cyclic pentyl groups, the various acyclic and cyclic hexyl groups, the various acyclic and cyclic heptyl groups, the various acyclic and cyclic octyl groups, etc. Typical examples of the lower alkyl, $C_{4-8}$-cycloalkyl, lower haloalkyl and $C_{4-8}$-halocycloalkyl substituents R' and R'' are the same as those alkyl and cycloalkyl groups above, except those having a tertiary $\alpha$-carbon atom, i.e., not having a hydrogen on the $\alpha$-carbon atom and, in the case of the haloalkyl and halocycloalkyl substituents, one or more halogen substituents on the carbon atoms of these alkyl groups, but not more than one halogen on the $\alpha$-carbon atom, e.g. chloromethyl, 1,2-dichloroethyl, 1,2-, 1,3-, 2,3-, 2,2-, 3,3-dichloropropyl, fluoromethyl, 1,2-dibromoethyl, etc.

R' and R'', together with the carbon to which they are attached can be a cyclohexyl ring including a lower alkyl substituted cyclohexyl ring, i.e., the ketone used is a cyclohexanone as contrasted to a cyclohexyl ketone or aldehyde which would result in either R' or R'' or both each being a cyclohexyl group, which can be substituted with one to five preferably one or two lower alkyl groups, i.e., the lower alkyl groups disclosed above. In addition, R'' but not R' can be phenyl or phenyl with one to five substituents preferably one to two lower alkyl groups, i.e., the lower alkyl groups previously disclosed and, when 2,6-diphenylthiophenol is used, and R' is hydrogen, R'' can be caboxyl, i.e., the carbonyl reactant is glyoxylic acid.

Typical but not limiting examples of some of the more readily available phenols and thiophenols falling within the above disclosure of the benzenoid compounds are: o-phenylphenol, 2,4- or 2,6-diphenylphenol, 2,4,6-triphenylphenol, 2-methyl-6-phenylphenol, 2-isopropyl-6-phenylphenol, 2-cyclohexyl-6-phenylphenol, 2-(2-biphenylyl)phenol, 2-(4-methylphenyl)phenol, phenylhydroquinone, 2-phenylresorcinol, 2,5-diphenylhydroquinone, etc., and the thio isologues of these phenols, e.g., o-phenylthiophenol, 2,6-diphenylthiophenol, phenylthiohydroquinone, etc.

Typical, but not limiting examples of some of the more readily available ketones and aldehydes falling within the above disclosure of the carbonyl compounds are: acetone, chloroacetone, acetaldehyde, methyl ethyl ketone, propionaldehyde, methyl octyl ketone, levulinic aldehyde (4-oxopentanal), octaldehyde (octanal), methyl cyclohexyl ketone, cyclobutanone, 6-bromo-2-hexanone, dicyclohexyl ketone, cyclohexanaldehyde, 2,3-dibromo-2-methylbutanal, 2-methyl-2,3-dichloropentanal, pentadecanal, cyclohexanone, 1,3- and 1,4-cyclohexadione, 2-ethylcyclohexanone, p-chlorobenzyl methyl ketone, acetophenone, benzaldehyde, diphenylacetaldehyde, 2,5-undecandione, $\alpha$-, o-, m- and p-chloroacetophenones, 1,4-dibenzoylbutane, o-, m- and p-diacetylbenzenes, o-, m- and p-niroacetophenones, o-, m- and p-chlorobenzaldehydes, m-bromobenzaldehyde, p-iodobenzaldehyde, o-, m- and p-fluorobenzaldehydes, terephthalaldehyde, adipicdialdehyde, 4,4-dicyclohexanone ([bicyclohexyl]-4,4'-dione), p-acetylbenzaldehyde, 4,4'-isopropylidenedicyclohexanone, etc.

Our process comprises reacting the desired benzenoid compound with the desired carbonyl compound in an acidic liquid phase in which the reactants are soluble and which is nonreactive with the other components, contains no more than 5 percent water and whose acid strength, as measured on the Hammett $H_o$ scale, is at least as strong as neat trifluoroacetic acid. On the Hammett $H_o$ scale, the values are called Hammett $H_o$ acidity functions and range from positive to negative numbers. The more negative the value, the stronger the acid. For a more complete discussion of the Hammett $H_o$ acidity functions, reference is made to the book "Acidity Functions" by Colin H. Rochester, Academic Press, New York (1970). This book and its references are hereby incorporated by reference for a teaching concerning acidity functions of various acids and the factors which govern acidity functions of various systems in which the acids are dissolved. The liquid phase can be either the neat acid having the required acid strength or it can be an inert organic liquid in which the acid is dissolved in sufficient quantity to give the desired acid strength.

Preferably, the liquid phase should be a solvent in which the amount of both reactants used are completely soluble. However, this is not a requisite, and heterogeneous reaction mixtures can be used when the reactants are sufficiently soluble in the liquid phase to give a reasonable reaction rate.

Typical but not limiting examples of acids that are readily available which we can use to provide the required acidity are: hydrogen fluoride, trifluoroacetic acid, mono-, di- and hexafluorophosphoric acids, fluoboric acid, methanesulfonic acid, trifluoromethanesulfonic acid, etc. Mixtures of these acids can be used but generally offer no advantage over the use of a single acid. Acids such as formic acid, acetic acid, the chloroacetic acids, are too weak to provide the required Hammett $H_o$ acidity function.

If desired, the acids, especially those having a very high negative Hammett $H_o$ activity function, can be diluted with a wide variety of organic liquids to provide the liquid phase still having the requisite acidity. By this means, the acidity of the reaction medium can be adjusted over a wide range to provide a particular value that is most suitable for producing the desired product under the optimum acidity condition. As is self-evident, the diluent should not be reactive with either the acid or reactants and must be miscible with the acid. Preferably, but not necessarily, the diluent should increase the solubility of the reactants in sthe liquid phase. Preferably, any inert organic liquid used as a diluent and solvent for the acid should be aprotic and should have a high dielectric constant since such a solution will have a higher negative Hammett $H_o$ activity function for a given acid than a solvent having a lower dielectric constant. Typical, but not limiting examples of readily available organic liquids we can use are: nitromethane, sulfolane, chloroform, chlorobenzene, o- or m-dichlorobenzene, the chlorotoluenes, nitorbenzene, etc. The particular solvent is not critical and its choice is dependent on the desires of the operator.

The rate of reaction of the carbonyl compound with the benzenoid compound is governed by the acidity of the organic reaction medium. The stronger the acidity, the faster the reaction. Likewise, heating will also speed up the rate of reaction. In the case of benzenoid compounds that can produce both dibenzopyrans and fluorenols, the initial product is the dibenzopyran. Longer reaction times, higher temperatures and increased acidity of the reaction medium, all favor the isomerization of the dibenzopyran to the corresponding fluorenol, providing the former is sufficiently soluble to permit isomerization to the latter. Example 30 illustrates the making of a dibenzopyran product under highly acidic conditions which would normally produce the fluorenol product. In this case, the dibenzopyran product was too insoluble in the reaction mixture to be isomerized. Thus, this is another technique to be used to control the type of product obtained.

When reacting benzenoid compounds that can produce both products, and dibenzopyrans are the desired product, in order to suppress isomerization to the fluorenol when heating the reaction mixture, we prefer to use trifluoroacetic acid, or one of the stronger acids which can be diluted with an inert solvent to about the same Hammett $H_o$ activity function, as the solvent medium. Such media have the minimum required acidity and minimize the formation of the other reaction products. Methanesulfonic acid is a good acid to use for reactions run at room temperature to produce dibenzopyrans.

In order to prepare the fluorenol compounds of this invention in highest yields and purity, except from monohydric phenols having only one phenyl or substituted phenyl substituent ortho to the phenolic hydroxyl group, we prefer to first form the dibenzopyran precursor and isolate it from the reaction mixture and then isomerize it in the absence of the carbonyl compound using any of the acidic media previously described, or Lewis acids, for example $AlCl_3$, $BF_3$ in trifluoroacetic acid, etc., can be used for the isomerization. In this way, the dibenzopyran can be converted completely into the desired fluorenol without causing any production of the higher condensed products. The above-excepted phenols will produce no product beyond the fluorenol in our reaction. Therefore, they can be prepared directly from the initial reactants using a very highly acidic liquid phase, for example, liquid anhydrous HF at room temperature.

Monitoring the reaction by vpc (vapor phase chromatograph), tlc (thin layer chromatography) and nmr (nuclear magnetic resonance spectrometry) will permit determining the optimum conditions to stop the reaction for maximum conversion of the reactant to the dibenzopyran and minimum formation of the fluorenol.

Surprisingly enough, the dibenzothiopyrans of this invention do not isomerize to the corresponding fluorenthiols. With these compounds, we therefore can use reaction media having higher acidity than trifluoroacetic acid with no danger of isomerization occurring. However, the thiophenols react quite rapidly with the carbonyl compounds and therefore trifluoroacetic acid is generally a convenient material to use as both acid and solvent. However, as will be illustrated in the examples, other acidic media having a higher acidity for example methanesulfonic acid alone or diluted with an inert solvent such as chlorobenzene, chloroform, etc., can be used.

Yields based on consumed reactants are very high for the dibenzopyrans, dibenzothiopyrans and fluorenols, and the unused reactants are readily recovered for reuse since our reaction is exceptionally free of side reactions. Where higher condensed products are produced they can be isolated as useful compounds.

Table I gives representative values of Hammett $H_o$ acidity functions of typical acids covering a wide range of values we can use and demonstrate the effect of dilution with water, a typical protolytic solvent, and nitromethane, a typical aprotic solvent. Percentages are by volume unless otherwise stated. The values of $H_o$ are not capable of being determined with extreme accuracy and are probably accurate to within ±0.5 units.

TABLE I

| Acid System | Hammett $H_o$ Acidity Function |
|---|---|
| Formic acid (ca. 2% by wt water) | −1.9 |
| Trifluoroacetic acid | −3.3 |
| Trifluoroacetic acid 5% water | −3.3 |
| Trifluoroacetic acid 10% water | −3.2 |
| Trifluoroacetic acid 15% water | −2.8 |
| Trifluoroacetic acid 30% water | −1.6 |
| Methanesulfonic acid (ca 2% by wt water) | −7.6 |
| Methanesulfonic acid 30% water | −3.6 |
| Methanesulfonic acid in 90% nitromethane | ca −7.0 |
| Difluorophosphoric acid | −8.9 |
| Difluorophosphoric acid in 95% nitromethane | −7.4 |
| Difluorophosphoric acid in 80% nitromethane | −8.8 |
| Hydrogen fluoride | −11.9 |
| Hydrogen fluoride with $BF_3$ | ca −15 |
| Hydrogen fluoride with $SbF_5$ | ca −17 |
| Trifluoromethanesulfonic acid | −14.0 |

In addition to the above effect of water, water also is a product of the dibenzopyran and dibenzothiopyran forming reaction. Therefore, the reaction is aided by using anhydrous liquid phase initially or at least limiting the amount of water present initially to no more than 5 percent by volume. Azeotropic distillation, use of inert desicants, etc., can also be used to remove the water of reaction but generally we have not found it necessary to remove the water of reaction.

In order that those skilled in the art may better understand our invention, the following examples are given by way of illustration and not by way of limitation. In all the examples, parts are by weight and temperatures are in degrees Centigrade unless otherwise specifically noted. Where elemental analyses are given for a named compound, the theoretical values calculated for this compound, are given in parentheses after the analytically determined values. The following abbreviations are used: tlc — thin layer chromatography, vpc — vapor phase chromatography, nmr — nuclear magnetic resonance (spectrometry).

The simpler dibenzopyrans and dibenzothiopyrans prepared in the following examples can be represented by the formula:

A. 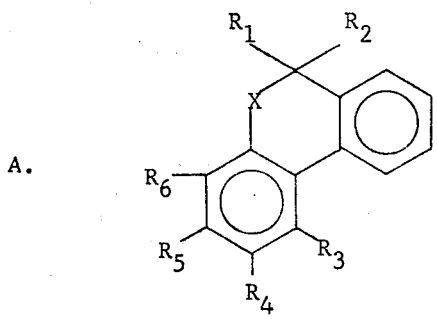

and the fluorenol isomers of the dibenzopyrans by the formula:

B. 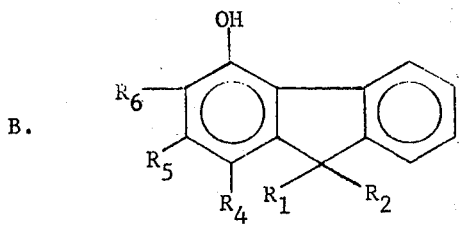

where X is oxygen or sulfur, $R_1$ and $R_2$, taken together, form a cyclohexyl ring, including lower alkyl substituted cyclohexyl ring with the carbon atom to which both are attached and, in addition, separately, R is hydrogen or lower alkyl free of a tertiary α-carbon atom and $R_2$ is lower alkyl free of a tertiary α-carbon atom, phenyl, lower alkyl substituted phenyl and, when X is sulfur and $R_1$ is hydrogen, carboxyl.

EXAMPLE 1

A mixture of 5.0 g. of 2,6-diphenylphenol, 10.0 ml. of acetone and 50.0 ml of trifluoroacetic acid was placed in a 250 ml ground bottom flask closed with a ground glass stopper and heated on a steam bath. Initially, the diphenylphenol was not completely soluble but did dissolve in the solution upon heating. At the end of 47.5 hours, the reaction mixture was poured into water, then extracted with chloroform. The organic layer was washed with a saturated aqueous sodium bicarbonate solution and dried with anhydrous sodium sulfate. After concentration of the organic layer, tlc and vpc showed no 2,6-diphenylphenol remaining and that there were four products present. After adding 2,6-diphenylphenol as a reference point, the vapor phase chromatograph obtained, showed that the four products, the simple dibenzopyran and fluroenol products shown in Equation I, and the more complex indenodibenzopyran and indenofluorenol products shown in Equation II, were present in the relative percentages of 54 percent, 5 percent, 23 percent and 18 percent respectively. Extraction of the reaction mixture with claisen's alkali extracts the two fluorenol products from the two dibenzopyran products. Distillation of the organic layer through an 18" spinning band column at less than 1 millimeter pressure permits the more complex dibenzopyran product of Equation II to be separated from the simpler dibenzopyran product of Equation I. The former is a white solid having a melting point of 112°–113°, whose structure, as shown in Equation II, was confirmed by nmr and mass spectrometry. Elemental analysis showed: C, 88.2 (88.3); H, 6.9 (6.8). All four of these products are better otained in reactions in which each is essentially the only product as will be illustrated in further examples.

In order to study the effect of acidity on the above reaction, various acidic media were used in the reaction of 2,6-diphenylphenol with representative carbonyl compounds. The various reaction mixtures were monitored for evidence of pyran formation with the following results: no pyran formation was noted for the reaction of 2,6-diphenylphenol with acetone in acetic acid saturated with hydrogen chloride, formic acid or formic acid saturated with hydrogen chloride. Some pyran formation was obtained when the acidic medium was an equal volume mixture of formic acid and trifluoroacetic acid. This system has a Hammett $H_o$ acidity function of approximately −2 and appears to represent the minimum or borderline acidity required for our reaction to proceed at all, and in order to have reasonable reaction rates it should be at least −3. As the ratio of trifluoroacetic acid to formic acid is increased, the rate of pyran formation is increased. Pyran formation was very evident in reactions of 2,6-diphenylphenol with acetone, benzaldehyde and cyclohexanone in acid systems such as 80 percent trifluoroacetic acid diluted with 20 percent chloroform, neat trifluoroacetic acid. 10 percent solution of difluorophosphoric acid in nitromethane and neat methane sulfonic acid. These percentages are by volume.

In another series of reactions involving the reaction of acetone and 2,6-diphenylphenol in trifluoroacetic acid, the effect of water in the initial reaction medium was studied. It was found that 2 percent by water caused a noticeable reduction in the rate and at 6 percent completely inhibited the reaction. On the other hand, trifluoroacetic anhydride which would react with the water formed in the reaction to form trifluoroacetic acid caused progressive enhancement of the rate of reaction up to about 5 volume percent with no further increase in the range of 5–10 percent.

In a series of reactions of paraldehyde and 2,6-diphenylphenol in trifluoroacetic acid, up to 3 percent water in the initial reaction mixture had no detectable effect. At the 6 percent water level, although the pyran reaction was not inhibited, it was very retarded and in this case some methylene-4,4'-bis(2,6-diphenylphenol) was produced.

In order to more closely study the effect of acidity on the rate of reaction, the following example was carried out:

EXAMPLE 2

To each of a series of 15 ml culture tubes having polytetrafluoroethylene lined screw caps was added 0.1000 g. of 2,6-diphenylphenol and 50 μl of cyclohexanone. Subsequently, 1.000 ml of nitromethane containing serially increasing amounts of difluorophosphoric acid was added. Each tube received a different concentration of acid as shown in Table II. Each tube was sealed, heated for 1 hr at 80° and quenched by addition of 10 ml of 0.1 percent aqueous KOH. 1 ml of nitromethane containing 50 mg/ml of m-terphenyl as a vpc standard was added to each tube. The tubes were shaken and the water layers removed. The remaining nitromethane solutions of products were washed with 0.1 percent KOH, distilled water, dried ($Na_2SO_4$) and placed in vials for vpc analysis. The results are shown in Table II.

TABLE II

| Tube No. | Vol. % $HPO_2F_2$ | $H_o$ | % Pyran | % Fluorenol |
|---|---|---|---|---|
| 1 | 0.99 | −2.4 | 0 | 0 |
| 2 | 1.96 | −3.3 | 7.5 | 0 |
| 3 | 2.91 | −4.2 | 17.6 | 0 |
| 4 | 3.85 | −4.9 | 30.7 | 0 |
| 5 | 4.76 | −5.5 | 48.1 | 0 |
| 6 | 5.66 | −6.0 | 62.7 | 0 |
| 7 | 6.54 | −6.5 | 72.5 | 0 |
| 8 | 7.40 | −6.7 | 83.9 | 0 |
| 9 | 8.26 | −7.1 | 89.1 | 0 |
| 10 | 9.09 | −7.3 | 92.5 | 0 |
| 11 | 20.00 | −8.8 | 60.2 | 39.8 |
| 12 | 30.00 | (a)~ | 50.2 | 49.8 |
| 13 | 40.00 | ~ | 61.2 | 35.4 |
| 14 | 50.00 | ~ | 75.2 | 14.9 |

(a)nitromethane-difluorophosphoric acid forms a two-phase system above ~25% difluorophosphoric acid.

From the data of Table II, it is evident that the threshold $H_o$ value for the pyran-forming reaction is approximately −3.0 and that the rate of the reaction increases almost linearly with more negative $H_o$ values. It can also be noted from Table II that the pyran reaction can be carried to essential completion in a rapid reaction with essentially no isomerization to the fluorenol by using acidic liquid media having a Hammett $H_o$ acidity function of about −7.5 or less and that negative values greater than this favor isomerization. The choice of temperature, time and acid concentration permits considerable control over the reaction of our carbonyl compounds with our benzenoid compounds. Difluorophosphoric acid is soluble in nitromethane to the extent of about 25%. The experiments in Table II carried out with 40 and 50 percent difluorophosphoric acid show a slightly decreased yield of products. This is thought to be due to unequal partitioning of the reactants between the two unstirred phases present in these experiments.

EXAMPLE 3

This example illustrates the faster reaction obtained by increasing the molar ratio of carbonyl compound to the benzenoid compound. In a series of eight reactions, 3.7 g. of 2,6-diphenylphenol was dissolved in 25 ml of refluxing trifluoroacetic acid. Sufficient acetone was added to these solutions to obtain molar ratios of acetone to phenol of 2:1, 3:1, 4:1, 6:1, 8:1 and 10:1, and 12:1. Samples were removed from the reactions at given times and analyzed by vpc. The amount of pyran in the reaction mixture, expressed as a mole fraction of the mixture was determined.

It was found that the amount of pyran produced after 30 minutes had approximately doubled, from 0.27 to 0.48, when the ratio of acetone to 2,6-diphenylphenol was doubled from 2:1 to 4:1 indicating a first order dependence on acetone concentration. From the same study, it was found that the rate of condensation could be increased by increasing acetone to 2,6-diphenylphenol ratio up to a ratio of approximately 6:1 and that above this ratio, the rate was retarded. The rate retardation occurring at the higher acetone concentrations is probably due to a buffering effect or reduction of the solution's acidity by the acetone. In these studies, the reaction to form the dibenzopyran was essentially complete in five hours when the ratio of acetone to 2,6-diphenylphenol was 6:1.

EXAMPLE 4

A solution of 370 g. of 2,6-diphenylphenol in 2 l. of trifluoroacetic acid was heated to reflux and 174 g. of acetone was added over a 10 minute period. After refluxing for 5.5 hours an additional 87 g. of acetone was added and reflux continued for an additional 0.5 hour. On cooling to room temperature, the crude 4-phenyl-6,6-dimethyl-6H-dibenzo[b,d]pyran, corresponding to formula A where X is oxygen, $R_1$ and $R_2$ are each methyl, $R_3$, $R_4$ and $R_5$ are each hydrogen and $R_6$ is phenyl, precipitated as a crystalline material which was filtered, washed with water and air dried. The product was dissolved in 1 l. of heptane containing 150 ml of toluene. The solution was extracted 3 times with 300 ml portions of Claisen's alkali to remove any phenolic bodies. After washing with water and drying over anhydrous magnesium sulfate, the solvent was removed under vacuum from the extracted heptane-toluene solution leaving a solid residue which was recrystallized from methanol to yield 281 g. of the purified dibenzopyran as white crystals having a melting point of 79°, whose structure was confirmed by infrared, nmr and mass spectrometry. Elemental analysis: C, 87.8 (88.1); H, 6.5 (6.3).

The mother liquors from the recrystallization of the above dibenzopyran always contain a second alkali insoluble material which could be separated from the above dibenzopyran by distillation at reduced pressure. A pure sample of this higher condensed product, the indenodibenzopyran whose structure is:

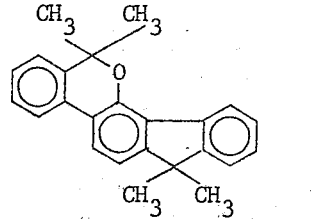

was obtained by fractional distillation under reduced pressure of less than 1 millimeter using an 18'' spinning band column. This product was obtained as a white solid having a melting point of 112°–113°. Its structure was confirmed by nmr and mass spectrometry. Elemental analysis showed: C, 88.2 (88.3); H, 6.9 (6.8).

EXAMPLE 5

A solution of 260 g. of the dibenzopyran produced in Example 4 dissolved in 1 l. of trifluoroacetic acid was heated at reflux for 11 days. After cooling to room temperature, 500 ml of water and 500 ml of heptane were added, causing a precipitate to form. Filtration yielded 46 g. of crystalline 9,9-dimethyl-3-phenyl-4-fluorenol, corresponding to formula B where $R_1$ and $R_2$ are each methyl, $R_4$ and $R_5$ are each hydrogen and $R_6$ is phenyl, which was washed with water and dried under vacuum. The heptane layer was extracted 3 times with Claisen's alkali and the alkali extracts combined and neutralized with aqueous hydrochloric acid to cause additional amount of the fluorenol to precipitate. It was recovered by filtration, washed with water and dried in a vacuum to yield an additional 71 g. of the above-named fluorenol. The total yield was 117 g. having a melting point of 106°–107°, and whose structure was confirmed by infrared, nmr and mass spectrometry.

Elemental analysis showed: C, 88.2 (88.1); H, 6.1 (6.3).

Isomerization of the dibenzopyran to the fluorenol was also effected by heating a solution of 1 g. of the dibenzopyran of Example 4 in 15 ml of chlorobenzene at 80° for 17 hours in the presence of 40 mg of aluminum chloride to yield 0.87 g. of the fluorenol. Isomerization could also be effected with other very strongly acidic media, for example methanesulfonic acid, liquid anhydrous HF, etc., or other Lewis acids, for example $BF_3$ in trifluoroacetic acid, etc. The fluorenol could also be isolated from the Claisen's alkali extraction layer of Example 4 by neutralization as described above in this example.

EXAMPLE 6

A solution of 2.8 g. of the fluorenol of Example 5 in 300 ml of trifluoroacetic acid was heated to reflux and 11.6 g. of acetone added over a 10 minute period. Analysis of the reaction mixture after a 2.5 hour period by vpc showed that the major component of the reaction mixture was the same indenodibenzopyran which was isolated in Example 4 from the mother liquors of the recrystallization step.

The reaction was allowed to proceed for a total of 14 hours by which time analysis by vpc showed that over 90 percent of the product was the indenofluorenol of Equation II. The acid was removed under vacuum and the solid residue dissolved in diethyl ether, washed 3 times with water and dried over anhydrous magnesium sulfate. After removal of the solvent under vacuum, the solid product was recrystallized from cyclohexane to yield 16.6 g. of the fluorenol having the structure:

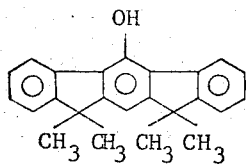

as white crystals having a melting point of 210°–211°. Its structure was confirmed by infrared, nmr and mass spectrometry. Elemental analysis showed: C, 88.5 (88.3); H, 6.9 (6.8).

EXAMPLE 7

A solution of 246 g. of 2,6-diphenylphenol in 1,250 ml of trifluoroacetic acid was heated to reflux and 200 g. of cyclohexanone added. After only 30 minutes of reaction at reflux there was a copious precipitate of spiro cyclohexane-1',6-(4-phenyl-6H-dibenzo[b,d]pyran), also known as 4-phenyl-6H-dibenzo[b,d]pyran-6-spiro-1'-cyclohexane, which was isolated by filtration of the hot reaction mixture and washed 3 times with water and dried in vacuum. After recrystallization from isopropanol, there was obtained 200 g. of the dibenzopyran as a white crystalline product having a melting point of 124°–125°, whose structure (corresponding to formula A where X is oxygen, $R_1$ and $R_2$ together with the carbon atom to which they are commonly attached, forms the cyclohexyl group, $R_3$, $R_4$ and $R_5$ are each hydrogen and $R_6$ is phenyl) was confirmed by infrared, nmr and mass spectrometry. Elemental analysis showed: C, 88.1 (88.3); H, 6.8 ( 6.8).

The dibenzopyran of this example was isomerized to its corresponding fluorenol by heating a solution of the dibenzopyran in chlorobenzene in the presence of $AlCl_3$ for 10 minutes. A 5 g. portion of this fluorenol was reacted with 3 g. of cyclohexanone in 50 ml of trifluoracetic acid and 5.6 g. of trifluoroacetic anhydride to produce the complex dibenzopyranofluorene having the formula:

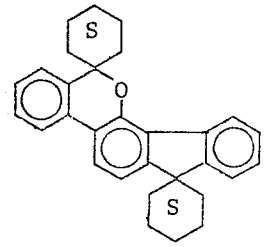

EXAMPLE 8

A solution of 150.1 g. of 2,6-diphenylphenol in 1 l. of trifluoroacetic acid was heated to reflux and 26.7 g. of paraldehyde added over a 15 minute interval. After refluxing for 1 hour, the solution was cooled, quenched with water and extracted with chloroform. The chloroform solution was washed with water, dried over anhydrous sodium sulfate and filtered. After removal of the chloroform under vacuum, the crude 6-methyl-4-phenyl-6H-dibenzo[b,d]pyran, corresponding to the formula A where X is oxygen, $R_1$, $R_3$, $R_4$ and $R_5$ are each hydrogen, $R_2$ is methyl, and $R_6$ is phenyl, was obtained as a brown oil. The oil was dissolved in a minimum amount of benzene and hexane added. The solution was extracted 5 times with 100 ml portions of Claisen's alkali after which the benzene-hexane solution was washed with water, dried and filtered. Removal of the solvent under vacuum, yielded 143.6 g. of the product as a clear brown oil which was found by vpc to be 81.3 percent of the desired dibenzopyran and 18.7 percent of a second product. The pure dibenzopyran was isolated by fractional distillation in an 18 inch spinning band column at less than 1 millimeter pressure. The liquid fraction collected at 180°–190° when treated with hexane produced white crystals of the pure product having a melting point of 61°–62°C., whose structure was confirmed by infrared and nmr spectroscopy. An elemental analysis showed: C, 88.0 (88.3); H, 6.0 (6.0). Molecular weight: 286 (272).

EXAMPLE 9

A solution of 100 g. of 2,6-diphenylphenol and 135 g. of benzaldehyde in 125 ml of chloroform and 500 ml of trifluoroacetic acid was maintained at 30° for 65 hours. During this time, 4,6-diphenyl-6H-dibenzo[b,d]pyran, corresponding to formula A where X is oxygen, $R_1$, $R_3$, $R_4$ and $R_5$ are each hydrogen and $R_2$ and $R_6$ are each phenyl, precipitated from the reaction mixture. It was washed 2 times with trifluoroacetic acid, 3 times with water and air dried. After recrystallization from ethanol, there was obtained 51.5 g. of the dibenzopyran as a white crystalline solid having a melting point of 102°–103°, whose structure was confirmed by infrared and nmr spectroscopy. Elemental analysis showed: C, 89.6 (89.8); H, 5.4 (5.4).

EXAMPLE 10

A suspension of 15 g. of 2,6-diphenylphenol in 150 ml of trifluoroacetic acid was heated to 50° and 7.07 g. of propanol (propionaldehyde) added. After 1 hour reaction at this temperature, the reaction mixture was quenched with water and extracted with benzene. The benzene layer was washed with water, diluted with hexane and extracted 3 times with 100 ml portions of Claisen's alkali. After washing with water and drying over anhydrous sodium sulfate and filtering, the solvent was removed from the benzene-hexane layer yielding 13.33 g. of 6-ethyl-4-phenyl-6H-dibenzo[b,d]pyran, corresponding to formula A where X is oxygen, $R_1$, $R_3$, $R_4$ and $R_5$ are each hydrogen, $R_2$ is ethyl and $R_6$ is phenyl, as a yellow oil which was shown by vpc to be 78 percent of the desired dibenzopyran. Preparative vpc was used to isolate the pure product as a yellow liquid whose structure was confirmed by infrared, nmr and ultraviolet spectrometry. Elemental analysis showed: C, 88.5 (88.1); H, 6.4 (6.3).

EXAMPLE 11

A suspension of 5.0 g. of 2,6-diphenylthiophenol and 140 ml of trifluoroacetic acid was heated to reflux and 5.8 g. of acetone added. The reaction mixture became pink and homogeneous after 2 minutes and after 5 minutes a clear oil had formed. After a total reaction time of 35 minutes, the mixture was cooled to room temperature and the solids which had precipitated, were filtered, washed several times with water and dried under vacuum at 50°. The crude product, 6,6-dimethyl-4-phenyl-6H-dibenzo[b,d]thiopyran, corresponding to formula A where X is sulfur, $R_1$ and $R_2$ are both methyl, $R_3$, $R_4$ and $R_5$ are each hydrogen and $R_6$ is phenyl, weighed 5.64 g. and was found by vpc to be greater than a 99 percent pure. Recrystallization from ethanol yielded white prisms of the product having a melting point of 124°–125° whose structure was confirmed by infrared, nmr and mass spectrometry. Elemental analysis showed: C, 83.2 (83.4); H, 6.1 (6.0).

EXAMPLE 12

A suspension of 5.0 g. of 2,6-diphenylthiophenol in 140 ml of trifluoroacetic acid was heated to reflux and 5.9 g. of cyclohexanone was added. The reaction mixture became homogeneous in 2 minutes. After refluxing for 2 hours and cooling to room temperature, the precipitate of the spiro cyclohexane-1′,6-(4-phenyl-6H-dibenzo[b,d]thiopyran), also known as 4-phenyl-6H-dibenzo[b,d]thiopyran-6-spiro-1′-cyclohexane, corresponding to formula A where X is sulfur, $R_1$ and $R_2$, together with the carbon atom to which both are attached, form the cyclohexyl group, $R_3$, $R_4$ and $R_5$ are each hydrogen and $R_6$ is phenyl, was isolated by filtration, washed several times with water and vacuum dried at 50°, yield 6.1 g. After recrystallization from benzene-isopropanol the product was obtained as white prisms having a melting point of 177°–178° whose structure was confirmed by infrared and nmr spectrometry. Elemental analysis showed; C, 84.2 (84.2); H, 6.6 (6.5). Molecular weight: 341 (342).

EXAMPLE 13

A solution of 3.0 g. of 2,6-diphenylthiophenol in 63 ml of trifluoroacetic acid was heated to reflux and 0.896 g. of glyoxylic acid added in small portions over a period of 5.5 hours. The reaction mixture was diluted with 200 ml of chloroform, washed 4 times with water and dried over anhydrous sodium sulfate and filtered. The solvent was evaporated to yield 3.73 g. of crude 6-carboxy-4-phenyl-6H-dibenzo[b,d]thiopyran, corresponding to formula A where X is sulfur, $R_1$, $R_3$, $R_4$ and $R_5$ are each hydrogen, $R_2$ is carboxyl and $R_6$ is phenyl. It was recrystallized from toluene to yield 0.557 g. of white crystals having a melting point of 201°–203° whose structure was confirmed by infrared and nmr spectrometry. Elemental analysis showed: C, 75.7 (75.5); H, 4.7 (4,4); S, 9.7 (10.0 ).

EXAMPLE 14

A mixture of 3.0 g. of 2,6-diphenylthiophenol and 2.0 g. of benzaldehyde in 10 ml of methanesulfonic acid and 20 ml of chlorobenzene was shaken vigorously for 15 minutes at room temperature. Analysis by vpc showed the reaction was complete in this short time. The acid and chlorobenzene layers were separated and the acid layer extracted with chloroform. The chloroform layer was combined with a chlorobenzene layer washed several times with water and the solvents removed by heating under vacuum. The solid residue weighing 3.8 g. was found by vpc and tlc to be essentially pure 4,6-diphenyl-6H-dibenzo[b,d]thiopyran, corresponding to formula A where X is sulfur, $R_1$, $R_3$, $R_4$ and $R_5$ are each hydrogen and $R_2$ and $R_6$ are each phenyl. After recrystallization from acetonitrile, this product was obtained as yellow crystals having a melting point of 162°–162.5° whose structure was confirmed by infrared, nmr and mass spectrometry. Elemental analysis showed: C, 85.6 (85.7); H, 5.3 (5.2).

EXAMPLE 15

A mixture of 1.0 g. of 2,6-diphenylthiophenol and 1.0 g. acetophenone in 5.0 ml of methanesulfonic acid and 6.0 ml of chlorobenzene was shaken vigorously for 5 hours at room temperature. After separating the acid layer from the chlorobenzene layer, it was extracted with 5 ml of chlorobenzene and the two chlorobenzene layers combined. After washing with water, the chlorobenzene was removed under vacuum giving 1.35 g. of essentially pure 6-methyl-4,6-diphenyl-6H-dibenzo[b,d]thiopyran which, after recrystallization from methanol, was a white crystalline solid having a melting point of 139°–139.5° whose structure, corresponding to formula A where X is sulfur, $R_1$ is methyl, $R_2$ and $R_6$ are each phenyl, and $R_3$, $R_4$ and $R_5$ are each hydrogen, was confirmed by infrared, nmr and mass spectrometry. Elemental analysis showed: C, 85.6 (85.7); H, 5.6 (5.5).

EXAMPLE 16

Although 2,4-diphenylphenol has 2 phenyl substituents, only 1 of them is ortho to the phenolic hydroxyl group. Therefore, it can form only the simple dibenzopyran and fluorenol since after the dibenzopyran has rearranged to the fluorenol, the phenyl substituent remaining is not ortho to the phenolic hydroxyl group of the fluorenol. A solution of 10.0 g. of 2,4-diphenylphenol in 100 ml of trifluoroacetic acid was heated to reflux and 2.36 g. of acetone added. After 220 minutes, another 2.36 g. of acetone was added and heating at reflux continued for an additional 130 minutes. The reaction mixture was cooled, quenched with water and extracted with benzene. After washing with water, the benzene layer was extracted 3 times with Claisen's alkali, washed with water and dried over anhydrous sodium sulfate. After evaporation of the benzene under vacuum, there was obtained 3.91 g. of 6,6-dimethyl-2-phenyldibenzo[b,d]pyran, corresponding to formula A where X is oxygen, $R_1$ and $R_2$ are each methyl, $R_3$, $R_5$ and $R_6$ are each hydrogen and $R_4$ is phenyl as a clear yellow oil which was shown to be greater than 99 percent pure by vpc and tlc. Its structure was confirmed by infrared and nmr spectroscopy. Elemental analysis showed: C, 88.0 (88.1); H, 6.4 (6.3). This pyran is readily isomerized to its corresponding fluorenol by further heating in trifluoroacetic acid.

EXAMPLE 17

2,3-diphenylphenol is a typical example of a phenol which will form a dibenzopyran but cannot isomerize to the fluorenol because the meta position involved in the isomerization reaction is already substituted with a phenyl group. A solution of 1.0 g. of 2,3-diphenylphenol, 1.0 g. of acetone, 25 ml of trifluoroacetic acid and 1.5 ml of trifluoroacetic anhydride were heated at reflux in dry air for 3.25 hours by which time a sample which was worked up with hexane in water to remove the acidic materials was shown by vpc to be free of the starting phenol. Approximately 98 percent of the material was insoluble in Claisen's alkali and 2 percent of the material was soluble in Claisen's alkali. Apparently the latter was the trifluoroacetic of 2,3-diphenylphenol. Heating of the reaction mixture at reflux was continued for 18 hours, but caused no detectable change in the reaction mixture. Extraction with hexane and washing with water of the reaction mixture and evaporation of the solvent isolated 0.99 g. of 1-phenyl-6,6-dimethyl-6H-dibenzo[b,d]pyran, corresponding to formula A where X is oxygen, $R_1$ and $R_2$ are each methyl, $R_3$ is phenyl and $R_4$, $R_5$ and $R_6$ are each hydrogen, as a viscous liquid which on standing in hexane for several days was isolated as a white crystalline compound. Its structure was confirmed by nmr spectroscopy. A sample of this material dissolved in anhydrous trifluoroacetic acid and refluxed for 23 hours did not produce any rearranged product. The phenyl substituent in the meta position of the initial phenyl had effectively prevented any rearrangement of the dibenzopyran to the fluorenol.

The simplest phenol which can participate in our reaction is 2-phenylphenol, also known as o-phenylphenol. It can only form the simple dibenzopyran or the simple fluorenol. The following several examples illustrate how the acidity of the reaction mixture can be used to control the reaction so that it either goes essentially completely to the formation of the dibenzopyran without formation of the fluorenol or goes completely to the fluorenol.

EXAMPLE 18

A solution of 15.0 g. of 2-phenylphenol and 10.3 g. of acetone in 100 g. of trifluoroacetic acid was heated at reflux for 48 hours. The reaction mixture was diluted with 300 ml of water and extracted with 150 ml of n-heptane. After washing several times with water the organic layer was extracted twice with Claisen's alkali, washed with water and dried over anhydrous sodium sulfate and passed through a column of alumina. Evaporation of the heptane yielded 12.4 g. of 6,6-dimethyl-6H-dibenzo[b,d]pyran corresponding to formula A where X is oxygen, $R_1$ and $R_2$ are each methyl and $R_3$, $R_4$, $R_5$ and $R_6$ are each hydrogen. It was obtained as a colorless oil whose structure was confirmed by infrared, nmr and mass spectrometry. Elemental analysis showed: C, 85.2 (85.7); H, 6.8 (6.7).

EXAMPLE 19

A solution of 10.0 g. of the above pyran in 36 ml of trifluoroacetic acid and 2.58 ml of water was heated at reflux for 130 hours. The reaction mixture was diluted with water and extracted with hexane. The organic layer was washed with water and extracted with Claisen's alkali. After neutralizing the aqueous alkaline solution, the oil which separated was diluted with hexane. After separating the hexane solution and drying over anhydrous magnesium sulfate, the solvent was removed on a rotary evaporator to yield 6.93 g. of 9,9-dimethyl-4-fluorenol having the structure of formula B wherein $R_1$ and $R_2$ are each methyl and $R_4$, $R_5$ and $R_6$ are each hydrogen. After recrystallization from hexane, the product melted at 87°–89° and its structure was confirmed by infrared and nmr spectrometry. Elemental analysis showed: C, 85.7 (85.7); H, 7.0 (6.7). Molecular weight: 217±11 (210).

EXAMPLE 20

The above fluorenol was prepared directly from 2-phenylphenol as follows: A mixture of 50.0 g. of 2-phenylphenol and 25.5 g. of acetone in a polyethylene reactor was cooled in an ice bath and approximately 450 ml of anhydrous hydrogen fluoride added. The reaction vessel was closed and the reaction mixture allowed to warm to room temperature. After only 20 minutes, analysis by vpc showed that all of the starting phenol had been consumed and that the product was essentially 1/3 of the dibenzopyran and 2/3 of the fluorenol. The reaction mixture was allowed to continue for 1.5 hours and quenched by pouring the reaction mixture onto ice. After extraction with chloroform, the organic layer was washed twice with water and dried over anhydrous sodium sulfate. After filtration, the solvent was evaporated yielding 60,4 g. of 9,9-dimethyl-4-fluorenol having the same structure as that obtained in the previous example, as a clear oil which crystallized upon standing. After recrystallization it had a melting point of 88° and its structure was confirmed by infrared, ultraviolet and mass spectrometry. Elemental analysis showed: C, 85.2 (85.7); H, 6.8 (6.7).

EXAMPLE 21

A mixture of 68 g. of 2-phenylphenol and 36.8 g. of chloroacetone was placed in a polytetrafluoroethylene bottle and cooled in an ice bath, after which 400 ml of anhydrous liquid hydrogen fluoride was added. After capping the bottle, it was allowed to warm to room temperature while stirring magnetically. After 2 hours, the reaction mixture was cautiously added to ice and the oily layer dissolved in chloroform. The organic layer was washed free of acid with water after which the solvent was evaporated under vacuum leaving 95 g. of 6-methyl-6-6-chloromethyl-6H-dibenzo[b,d]-pyran as an oil whose formula corresponds to that of formula A where X is oxygen, $R_1$ is methyl, $R_2$ is chloromethyl and $R_3$, $R_4$, $R_5$ and $R_6$ are each hydrogen. An attempt to extract a benzene-hexane solution of the product with Claisen's alkali proved unsuccessful due to difficulties in separating the aqueous from the organic layer, necessitating reclamation of the product from this mixture. The reclaimed product was fractionally distilled at a reduced pressure of 2 mm to yield 29 g. of the product as a clear oil distilling at 150±2°. Its structure was confirmed by ultraviolet, nmr and mass spectrometry. Elemental analysis showed: C, 73.0 (73.6); H, 5.3 (5.4).

EXAMPLE 22

After adding 0.98 g. of cyclohexanone to a solution of 1.71 g. of 2-phenylphenol in 15 ml of trifluoroacetic acid, the reaction mixture was heated at 66° for 3.5 hours. The reaction mixture was diluted with 100 ml of water and extracted with chloroform. After washing the organic layer twice with water, once with saturated aqueous sodium bicarbonate and again with water, it was dried over anhydrous magnesium sulfate and the solvent evaporated. The residue was dissolved in n-heptane, the solution extracted twice with Claisen's alkali, washed twice with water and dried over anhydrous magnesium sulfate. After evaporation of the heptane under vacuum, there was obtained 1.42 g. of spiro(cyclohexane-1', 6(6H)dibenzo[b,d]pyran), also known as 6H-dibenzo[b,d]pyran-6-spiro-1'-cyclohexane, whose structure corresponds to that of formula A where X is oxygen, $R_1$ and $R_2$ together with the carbon atom to which they are commonly attached, forms the cyclohexyl group, and $R_3$, $R_4$, $R_5$ and $R_6$ are each hydrogen. It was a white crystalline solid having a melting point of 83.5°–84.3° whose structure was confirmed by infrared, nmr and mass spectrometry. Elemental analysis showed: C, 86.4 (86.4); H, 7.5 (7.3).

This dibenzopyran was readily converted to its corresponding fluorenol by heating a solution of the dibenzopyran in chlorobenzene in the presence of aluminum chloride.

The next examples again illustrate the ease with which acidity is used to control whether a dibenzopyran or fluorenol is obtained. In these examples, an aryl alkyl ketone will be used.

EXAMPLE 23

A solution of 1.7 g. of 2-phenylphenol and 1.545 g. of p-chloroacetophenone in 45 ml of nitromethane was prepared and 45 ml of difluorophosphoric acid was added. The reaction was stirred at room temperature for 21 hours at which time analysis by vpc showed that about 90 percent of the phenol had been converted and that the products of the conversion were 85 percent, 6-methyl-6-p-chlorophenyl-6H-dibenzo[b,d]pyran having the structural formula A where X is oxygen, $R_1$ is methyl, $R_2$ is p-chlorophenyl and $R_3$, $R_4$, $R_5$ and $R_6$ are each hydrogen, and 15 percent, 9-p-chlorophenyl4-fluorenol whose structure corresponds to formula B where $R_1$ is methyl, $R_2$ is p-chlorophenyl and $R_4$, $R_5$, and $R_6$ are each hydrogen. The reaction mixture was poured into water and extracted with chloroform. The organic layer was washed with water and then evaporated to dryness. The product was dissolved in a minimum amount of benzene and hexane added. The solution was extracted 3 times with 10 ml portions of Claisen's alkali. Analysis by vpc showed that the organic layer was free of the fluorenol which had been extracted into the aqueous alkaline solution. After drying the organic layer over anhydrous sodium sulfate and filtering, the organic solvents were evaporated yielding 1.6 g. of an oil which crystallized. The product was dissolved in methanol, treated with charcoal, filtered and cooled to produce white needles of the dibenzopyran having a melting point of 97° whose structure was confirmed by infrared, ultraviolet, nmr and mass spectrometry. Elemental analysis showed: C, 78.2 (78.3); H, 5.1 (4.9). The fluorenol can be recovered from the alkaline aqueous solution by neutralization as described in Example 5.

Similar results were obtained when equivalent amounts of acetophenone, p-methylacetophenone and m-hydroxyacetophenone were substituted for the p-chloroacetophenone in the above reaction.

EXAMPLE 24

A mixture of 16.5 g. of p-nitroacetophenone and 17.3 g. of 2-phenylphenol in a polyethylene bottle was cooled in an ice bath and 150 ml of liquid anhydrous hydrogen fluoride added. After tightly capping the bottle, the reaction mixture was allowed to warm to room temperature while stirring magnetically and reaction allowed to proceed for 20 hours. The hydrogen fluoride was removed with a stream of nitrogen. The residual white solid was dissolved in chloroform and the solution washed with water and dried over anhydrous magnesium sulfate. Hexane was added to the solution to precipitate the product which was filtered and vacuum dried. There was obtained 29.1 g. of 9-methyl-9-pnitrophenyl-4-fluorenol having a structure of formula B where $R_1$ is methyl, $R_2$ is p-nitrophenyl and $R_4$, $R_5$ and $R_6$ are each hydrogen. It was a white crystalline solid having a melting point of 185.7°–186.7° whose structure was confirmed by infrared, nmr and mass spectrometry. Its equivalent weight as determined by titration with tetrabutylammonium hydroxide in pyridine was a 310 (317). Elemental analysis showed: C, 75.8 (75.7); H, 4.9 (4.8); N, 4.5 (4.4).

EXAMPLE 25

A mixture of 17.0 g. of 2-phenylphenol and 16.5 g. of m-nitroacetophenone in a polyethylene bottle was cooled in an ice bath while 150 ml of liquid anhydrous hydrogen fluoride was added. After capping of the bottle, it was allowed to warm to room temperature while the reaction mixture was magnetically stirred. After a 4 hour reaction period, the hydrogen fluoride was removed with a stream of nitrogen and 200 ml of water and 100 ml of chloroform added. The solids which formed were filtered, washed several times with water and dried in a vacuum oven. There was obtained 27 g. of 9-methyl-9-m-nitrophenyl-4-fluorenol whose structure corresponds to that of formula B wherein $R_1$ is methyl, $R_2$ is m-nitrophenyl and $R_4$, $R_5$, and $R_6$ are each hydrogen. An additional 3 grams of product which were shown to be greater than 90 percent fluorenol by vpc was isolated from the chloroform solution. After recrystallization from hot chloroform the fluorenol was obtained as a slightly yellow crystalline solid having a melting point of 178°–178.8°, whose structure was confirmed by infrared, nmr and mass spectrometry. Its equivalent weight as determined by titration with tetrabutylammonium hydroxide in pyridine was 310 (317). Elemental analysis showed: C, 75.8 (75.7); H, 4.9 (4.8); N, 4.4 (4.4).

The nitro groups of the above two nitrophenylfluorenols can be readily reduced to amino groups by hydrogenation in the presence of a platinum oxide hydrogenation catalyst. THe hydrogenation proceeds readily under a hydrogen pressure of 30 psi using absolute ethanol as the solvent for the fluorenols. Likewise, the hydroxyl group of the fluorenol is readily esterified by acids to produce esters, for example, the acetate is readily prepared by dissolving the fluorenol in acetic anhydride and adding a small amount of pyridine.

EXAMPLE 26

A solution of 38 g. of 2-phenylphenol in 500 ml of trifluoroacetic acid was heated to reflux and 10 g. of 1,4-cyclohexanedione was added. After refluxing for 3 hours, the reaction mixture was cooled and filtered to yield 7.25 g. of the bis(dibenzopyran) having the formula,

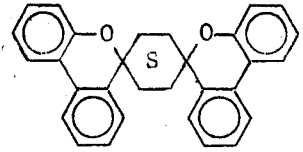

as a white crystalline solid having a melting point of 292°–293°. After recrystallization from toluene, the melting point was raised to 293°–294°. Its structure was confirmed by infrared, nmr and mass spectrometry. Elemental analysis showed: C, 86.7 (86.5); H, 5.8 (5.8).

EXAMPLE 27

A solution of 17.02 g. of 2-phenylphenol and 8.11 g. of m-diacetylbenzene in 90 ml of nitromethane was prepared and 10 ml of distilled difluorophosphoric acid added. After heating for 2 hours at 80°, the reaction mixture was quenched by adding water and then diluting with chloroform. After separating the organic layer, it was washed 3 times with water and dried over anhydrous sodium sulfate. After the solvent was removed under vacuum, the residue was dissolved in hexane containing the minimum amount of chloroform to dissolve it and chromatographed on silica using portions of hexane-chloroform mixtures of increasing chloroform content as eluent. The first fraction, after evaporation of the solvent, weighed 3 g. and was identified by nmr, ultraviolet and mass spectrometry as the bis(dibenzopyran) having the formula,

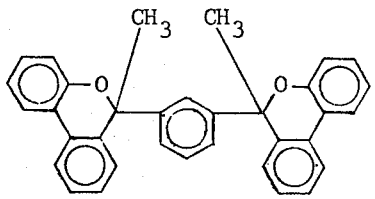

Elemental analysis showed: C, 87.9, 88.1 (87.5); H, 5.7, 5.9 (5.62).

A second material was eluted after the above bis(dibenzopyran), whose nmr spectrum showed it to be 6-(4-acetylphenyl)-6-methyl-6H-dibenzopyran resulting from the reaction product of 1 mole of the phenol with 1 mole of the diketone.

EXAMPLE 28

A mixture of 20 g. of 2-phenylphenol, 8.1 g. of mdiacetylbenzene and 100 ml of diethylether was placed in a 500 ml polytetrafluoroethylene bottle. After cooling to 0° 400 ml of liquid, anhydrous hydrogen fluoride was added, the bottle capped tightly and the contents stirred vigorously with a magnetic stirrer as it warmed to room temperature. Samples were taken periodically and analyzed by thin layer chromatography which indicated that after 20 hours the reaction was actually 95 percent complete for the conversion to the bisfluorenol. The reaction mixture was cooled and then poured onto ice and the organic phase diluted with chloroform. After separating the organic layer, washing with water and drying over anhydrous magnesium sulfate, the solvents were evaporated under vacuum to yield 23.4 g. of a tan somewhat tacky solid product which was shown to be greater than 99 percent of the pure bisfluorenol having the structure,

HO—⟨⟩—C(CH₃)—⟨⟩—C(CH₃)—⟨⟩—OH

The product was further purified by chromatography on a silica gel column using chloroform as the eluent. The product was isolated as a white crystalline solid having a melting point of 211°–214°, whose structure was confirmed by infrared, nmr and mass spectrometry. Elemental analysis showed: C, 87.6 (87.5); H, 5.9 (5.6).

EXAMPLE 29

A solution of 40.0 g. of 2-chloro-6-phenylphenol in 11.35 g. of acetone and 250 ml of trifluoroacetic acid was refluxed in dry air. After 48 hours, an additional 11.35 g. of acetone was added and heating at reflux continued for an additional 67 hours. The reaction mixture was diluted with water, extracted with hexane and the organic layer extracted with Claisen's alkali. The organic layer was then evaporated yielding 15.26 g. of 4-chloro-6,6-dimethyl-6H-dibenzo[b,d]-pyran as a viscous liquid which was shown to be greater than 99 percent pure by vpc. Its structure was confirmed by infrared, nmr and mass spectrometry. Elemental analysis showed: C, 73.1 (73.6); H, 5.2 (5.4); Cl, 14.2 (14.5).

EXAMPLE 30

A solution of 1.0 g. of 2,5-diphenylhydroquinone in 5 ml of diethyl ether and 0.67 g. of acetone in a polytetrafluoroethylene bottle was cooled to 15° and 20 ml of anhydrous liquid hydrogen fluoride added. The reaction mixture was stirred at this temperature for 8 hours during which time the product had precipitated yielding a heterogeneous reaction mixture. The reaction mixture was poured onto crushed ice. After the ice had melted, the mixture was extracted with chloroform. The chloroform solution was washed 3 times with water, dried over anhydrous sodium sulfate and then the solvent evaporated. The residue was dissolved in refluxing carbon tetrachloride from which the benzopyranodibenzopyran product having the structural formula,

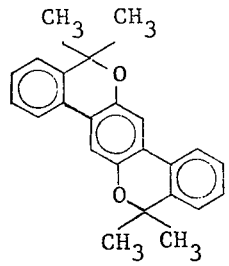

was obtained as a white crystalline material weighing 0.52 g. having a melting point of 231°–230° whose structure was confirmed by infrared, nmr and mass spectrometry. Elemental analysis showed: C, 84.6 (84.2); H, 6.3 (6.5).

This product can be isomerized to the corresponding benzopyranofluorenol and indenofluorendiol products by further reaction of a solution of the above product under the prescribed conditions or by use of a Friedel-Crafts catalyst as described in Example 5.

EXAMPLE 31

A solution of 1.0 g. of 2-methyl-6-phenylphenol and 1.19 g. of acetone in 10 ml of trifluoroacetic acid was heated at 62°–65° for 6.25 hours. The reaction mixture was diluted with water and extracted with n-heptane. The organic layer was extracted 3 times with Claisen's alkali, washed twice with water, dried over anhydrous magnesium sulfate and the solvent evaporated to yield 0.90 g. of 4,6,6-trimethyl-6H-dibenzo[b,d]pyran as a colorless oil. Its structure was confirmed by infrared, nmr and mass spectrometry. Elemental analysis showed: C, 85.7 (85.7); H, 7.2 (7.1).

This pyran was readily converted to 3,9,9-trimethyl-4-fluorenol by heating a solution of 5 grams of the dibenzopyran in 84 ml of trifluoroacetic acid and 7 ml of water at reflux for 46 hours. It was obtained in a yield of 4.45 g. as a viscous liquid shown to be homogeneous by vpc. Its structure was confirmed by nmr and infrared spectrometry. Elemental analysis showed; C, 85.2 (85.7); H, 7.2 (7.2).

EXAMPLE 32

A solution of 50 g. of 2-methyl-6-phenylphenol in 400 ml of trifluoroacetic acid was heated to reflux and 10 g. of 1,4-cyclohexanedione was added. After heating at reflux for 1 hour, the reaction mixture was filtered to yield 10.82 g. of the product having a melting point of 300°–301°. The filtrate was returned to the reaction flask and refluxed an additional 3 hours to yield an additional 6.2 g. of product having a melting point of 294°–298°. The 2 precipitates were combined and recrystallized from hot chloroform to yield 13.1 g. of the bis(dibenzopyran) having the formula,

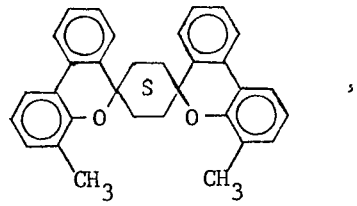

as a white crystalline solid having a melting point of 302°–303° whose structure was confirmed by infrared, ultraviolet, nmr and mass spectrometry. Elemental analysis showed: C, 86.8 (86.5); H, 6.4 (6.3).

EXAMPLE 33

A solution of 3.68 g. of 2-methyl-6-phenylphenol in 50 ml of trifluoroacetic acid was heated to reflux and 1.94 g. of 4,4'-bicyclohexanone, also known as [bicyclohexyl]-4,4'-dione, was added. After heating at reflux for 35 minutes, the reaction mixture was cooled and filtered, the precipitate washed with trifluoroacetic acid and then methanol after which it was dried. A yield of 3.1 g. of crude material was obtained which was recrystallized from benzene to give 2.77 g. of the bis(dibenzopyran) having the structure,

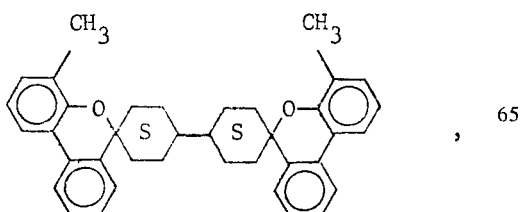

having a melting point of 272°–273° and whose structure was confirmed by infrared, ultraviolet, nmr and mass spectrometry. Elemental analysis showed: C, 86.2 (86.6); H, 7.3 (7.3).

EXAMPLE 34

A mixture of 46.05 g. of 2-methyl-6-phenylphenol and 23.64 g. of 4,4'-isopropylidenedicyclohexanone was prepared and 500 ml of trifluoroacetic acid added at room temperature. The reaction mixture was heated at reflux for 1.5 hours, cooled to room temperature and filtered yielding 54.6 g. of a white crystalline product. Recrystallization from hot toluene gave 38.79 g. of the bis(dibenzopyran) having the structure,

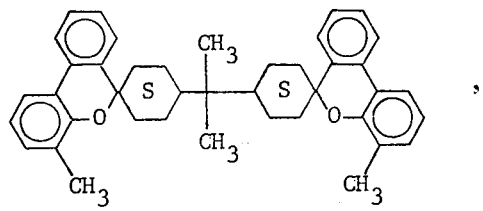

whose melting point was 272°–273°. Its structure was confirmed by infrared, ultraviolet, nmr and mass spectrometry. Elemental analysis showed: C, 86.3 (86.5); H, 7.7 (7.8).

EXAMPLE 35

In addition to being able to convert a bis(dibenzopyran) of this invention to their corresponding bisfluorenols using the acidic conditions used in preparing the bis(dibenzopyrans), Lewis acids, for example, aluminum chloride, can also be used as shown by this example. A solution of 20 g. of the bis(dibenzopyran) of Example 34 in 200 ml of chlorobenzene was prepared and 1.5 g. of aluminum chloride was added. The reaction mixture was maintained at 60° with stirring overnight. Analysis by tlc showed that the reaction was essentially complete. A saturated aqueous solution of ammonium chloride was added to quench the reaction. The organic layer was separated, washed and the solvent evaporated. The residue was dissolved in a minimum amount of hot toluene and allowed to stand. The crystalline precipitate which was isolated by filtration, washing and drying, weighed 4 g. and had a melting point of 276°–278°. Infrared, nmr and mass spectrometry confirmed that it was the bisfluorenol having the formula,

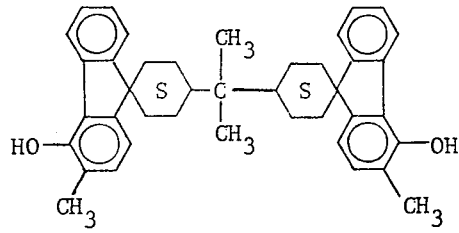

Elemental analysis showed: C, 86.7 (86.6); H, 7.9 (7.8).

EXAMPLE 36

A mixture of 5 g. of 2-cyclohexyl-6-phenylphenol and 2.34 g. of 4,4'-isopropylidenedicyclohexanone was prepared and 75 ml of trifluoroacetic acid added at room temperature. The pink solution was heated to reflux causing a light grey precipitate to form within 7 minutes. After heating an additional 1.4 hours at reflux, the mixture was cooled and filtered yielding a light grey crystalline material which was recrystallized from hot toluene to yield 3.8 g. of the bis(dibenzopyran) having the formula,

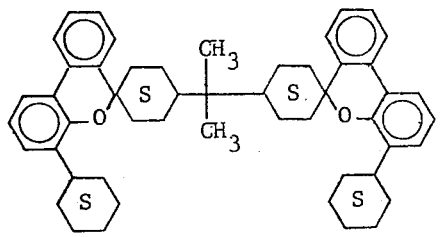

whose melting point was 259°–261°. Its structure was confirmed by infrared, ultraviolet, nmr and mass spectrometry. Elemental analysis showed: C, 86.6 (86.9); H, 8.3 (8.6).

EXAMPLE 37

This example illustrates how the dibenzopyrans of this invention can be converted to a phenol which is the same as the phenol from which the dibenzopyran was formed except that it now has a substituent in the ortho position of the phenyl substituent which is characteristic of the carbonyl compound used in making the dibenzopyran. A mixture of 10.0 g. of spiro(cyclohexane-1',6(6H)dibenzo[b,d]pyran), prepared in Example 22 and 0.5 g. of carbon black on which had been deposited 10 percent palladium was heated under a nitrogen atmosphere at about 305° for 17 hours. Analysis of a sample by vpc at this time showed 50 percent of the starting dibenzopyran. Heating was continued for 7 days at which time analysis by vpc showed essentially only one product. After filtering the reaction mixture which had been dissolved in hexane, it was extracted by Claisen's alkali and isolated from the alkali solution by acidification. There was obtained 5.15 g. of a viscous liquid phenolic compound which was shown by vpc to be about essentially 97 percent pure o-(2-biphenylyl)-phenol, also known as 2-hydroxy-o-terphenyl, whose structure,

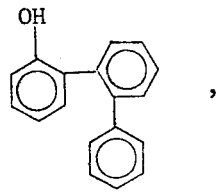

was confirmed by nmr spectroscopy. This phenol, like the other phenols of this invention, can likewise be reacted with carbonyl compounds to convert it to a dibenzopyran.

As shown above, many of the dibenzopyrans can be isomerized to the fluorenols or the pyran ring, like the thiopyran ring can be cleaved so that the dibenzopyran and dibenzothiopyrans of this invention can be converted to phenols having a phenol substituent in the ortho position which itself is substituted in its ortho position with a substituent which is dependent upon the carbonyl compound used initially in making the pyran. This cleavage can be accomplished either chemically or electrochemically and is preferably carried out electrochemically for the thiopyrans. The spirodibenzopyrans likewise can be dehydrogenated, for example with palladium, platinum or other dehydrogenation catalyst as illustrated above, which simultaneously converts the cyclohexyl group to a phenyl group and cleaves the pyran ring to produce phenols again having a phenyl substituent ortho to the phenolic hydroxyl group which itself is substituted with a phenyl group in its ortho position. These phenols and thiophenols as well as the fluorenols are phenolic bodies which can be used as stabilizers and antioxidants to prevent polymerization of polymerizable polymers as well as additives for lubricating oils to impart antioxidation properties to the lubricants.

The above examples have shown some of the variations which are possible with our invention. Other obvious variations will be apparent to those skilled in the art in light of the above teachings. For example, other compounds having ketonic and/or aldehydic carbonyl groups can be substituted for the particular aldehydes and ketones specifically used. All such variations are within the full intended scope of the invention as defined by the appended claims. The products in the examples using diketones can be one of several or a mixture of stereoisomers of the actual formulae given.

What we claim as new and desire to secure by Letters Patent of the United States is:

1. A process of producing a dibenzo [b,d] pyran of the formula

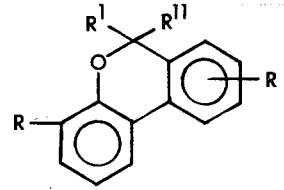

where R is hydrogen, lower alkyl, $C_{4-8}$-cycloalkyl or phenyl, $R^1$ and $R^{11}$, taken together with the carbon atom to which both are attached, is cyclohexyl or lower alkyl substituted cyclohexyl, and, individually, $R^1$ is hydrogen, lower alkyl, $C_{4-8}$-cycloalkyl, lower haloalkyl or $C_{4-8}$-halocycloalkyl, wherein the α-carbon atom of said R and $R^1$ substituents, other than the hydrogen, has at least one hydrogen and no more than one halogen, and $R^{11}$ is alkyl, cycloalkyl, haloalkyl or halocycloalkyl as defined for $R^1$ and, in addition, phenyl or substituted phenyl wherein the substituents are lower alkyl, $C_{4-8}$-cycloalkyl, halo or nitro, there being no more than one nitro group on any one phenyl ring comprising the reaction of (A) a benzenoid compound of the formula

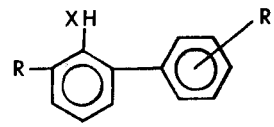

where R is as previously defined, X is oxygen, and (B) a carbonyl compound having no more than 20 carbon atoms, the carbonyl group being ketonic or formyl, said compound having the formula

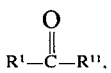

where $R^1$ and $R^{11}$ are as defined above, subject to the proviso (C) that the benzenoid compound is reacted with the carbonyl compound in an acidic liquid phase (a) which is nonreactive with the (A) and (B) compounds (b) in which the (A) and (B) compounds are soluble, (c) which contains no more than 5% water by volume, and (d) whose acid strength, as measured on the Hammett $H_O$ scale is at least as strong as neat trifluoroacetic acid.

2. The process of claim 1, wherein the benzenoid compound A is o-phenylphenol.

3. The process of claim 1, where the benzenoid compound A is 2-methyl-6-phenylphenol.

4. The process of claim 1, where the benzenoid compound A is 2-chloro-6-phenylphenol.

5. The process of claim 1, where the benzenoid compound A is 2,6-diphenylphenol.

6. The process of claim 1, wherein the carbonyl compound B is an aldehyde having formula I.

7. The process of claim 1, wherein the carbonyl compound B is a ketone having formula I.

8. The process of claim 1, wherein the carbonyl compound B is a ketone having formula I where R' is lower alkyl and R'' is phenyl.

9. The process of claim 1, wherein the carbonyl compound B is a ketone having formula I where R' and R'' are each lower alkyl.

10. The process of claim 1, wherein trifluoroacetic acid is used to obtain the desired acidity.

11. The process of claim 1, where the Hammett $H_0$ value is at least approximately —3.0.

12. A process of producing a fluoren-4-ol of the formula

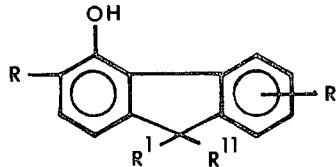

wherein R, R', R'' are as previously defined, which comprises isomerizing a dibenzo[b,d]pyran of claim 3, under isomerization reaction conditions.

13. The process of claim 12, where the Hammett $H_0$ value is at least approximately —7.5.

14. The process of claim 12, where the Hammett $H_0$ value is at least as strong as hydrogen fluoride.

15. The process of claim 12, where the Hammett $H_0$ value is at least as strong as difluorophosphoric acid.

16. A process of producing a dibenzothio[b,d]pyran of the formula

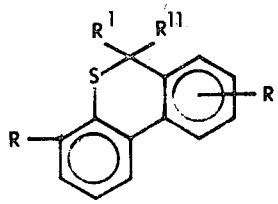

where R' is hydrogen, R'' is carboxy, R being as previously defined comprising the reaction of (A) a benzenoic compound of the formula

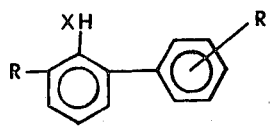

where R being as previously defined and X is sulfur and (B) glyoxylic acid, subject to the proviso (C) that the benzenoid compound is reacted with the carbonyl compound in an acidic liquid phase (a) which is nonreactive with the (A) and (B) compounds, (b) in which the (A) and (B) compounds are soluble, (c) which contains no more than 5% water by volume, and (d) whose acid strength, as measured on the Hammett $H_0$ scale is at least as strong as neat trifluoroacetic acid.

17. The process of claim 16, where the benzenoid compound A is 2,6-diphenylthiophenol.

18. A process of producing a fluoren-4-thiol of the formula

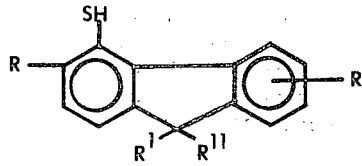

where R, R', R'' are as previously defined, which comprises isomerizing a dibenzothiopyran of claim 16 under isomerization reaction conditions.

* * * * *